(12) United States Patent
Kao et al.

(10) Patent No.: US 9,289,159 B2
(45) Date of Patent: Mar. 22, 2016

(54) USER IDENTIFICATION METHOD, PHYSIOLOGICAL DETECTION DEVICE AND PHYSIOLOGICAL DETECTION METHOD

(71) Applicants: Ming-Tsan Kao, Hsin-Chu (TW); Sen-Huang Huang, Hsin-Chu (TW); Ren-Hau Gu, Hsin-Chu (TW); Chung-Yuo Wu, Hsin-Chu (TW)

(72) Inventors: Ming-Tsan Kao, Hsin-Chu (TW); Sen-Huang Huang, Hsin-Chu (TW); Ren-Hau Gu, Hsin-Chu (TW); Chung-Yuo Wu, Hsin-Chu (TW)

(73) Assignee: PIXART IMAGING INC., Hsin-Chu County (TW)

( * ) Notice: Subject to any disclaimer, the term of this patent is extended or adjusted under 35 U.S.C. 154(b) by 507 days.

(21) Appl. No.: 13/869,368

(22) Filed: Apr. 24, 2013

(65) Prior Publication Data

US 2014/0323835 A1    Oct. 30, 2014

(30) Foreign Application Priority Data

May 1, 2012 (TW) .............................. 101115437 A

(51) Int. Cl.
| | |
|---|---|
| *G05B 19/00* | (2006.01) |
| *A61B 5/117* | (2006.01) |
| *A61B 5/11* | (2006.01) |
| *G06K 9/00* | (2006.01) |
| *G06K 9/62* | (2006.01) |
| *A61B 5/1455* | (2006.01) |
| *A61B 5/024* | (2006.01) |

(52) U.S. Cl.
CPC .............. *A61B 5/117* (2013.01); *A61B 5/1122* (2013.01); *G06K 9/00006* (2013.01); *G06K 9/00885* (2013.01); *G06K 9/624* (2013.01); *A61B 5/02444* (2013.01); *A61B 5/14552* (2013.01)

(58) Field of Classification Search
CPC .. A61B 5/02444; A61B 5/1122; A61B 5/117; A61B 5/14552; G06K 9/00006; G06K 9/00885; G06K 9/624
See application file for complete search history.

(56) References Cited

U.S. PATENT DOCUMENTS

| | | | |
|---|---|---|---|
| 7,072,701 B2 | 7/2006 | Chen et al. | |
| 2003/0028784 A1 | 2/2003 | Uchida | |
| 2008/0113791 A1* | 5/2008 | Williams | G06F 21/31 463/29 |
| 2009/0138207 A1* | 5/2009 | Cosentino | A61B 5/14532 702/19 |
| 2009/0210939 A1* | 8/2009 | Xu | G06K 9/00154 726/19 |
| 2012/0110470 A1* | 5/2012 | Mistry | G06F 3/0488 715/748 |
| 2012/0284195 A1* | 11/2012 | McMillen | G06Q 20/3223 705/71 |
| 2012/0319816 A1* | 12/2012 | Al-Ali | A61B 5/14551 340/5.8 |
| 2013/0072771 A1* | 3/2013 | Gu | A61B 5/0205 600/324 |
| 2013/0127714 A1* | 5/2013 | Gu | A61B 5/6898 345/158 |
| 2013/0127721 A1* | 5/2013 | Gu | G06F 3/033 345/166 |
| 2013/0131473 A1* | 5/2013 | Gu | G06F 3/0421 600/324 |
| 2014/0343462 A1* | 11/2014 | Burnet | A61B 5/1101 600/595 |

FOREIGN PATENT DOCUMENTS

TW       201134453 A1    10/2011

* cited by examiner

*Primary Examiner* — Ojiako Nwugo
(74) *Attorney, Agent, or Firm* — Hauptman Ham, LLP

(57) ABSTRACT

There is provided a physiological detection device including a finger detection unit, a storage unit and a processing unit. The finger detection unit is configured to detect a current track drawn by a current user and current physiological information of the current user. The storage unit is configured to previously store track features of predetermined tracks drawn, for a predetermined time interval or a predetermined times on the finger detection unit, by a plurality of users and each of the track features is associated with one of the users. The processing unit is configured to analyze the current track and identify the current user according to the track features in the storage unit. There is further provided a physiological detection method and a user identification method.

17 Claims, 6 Drawing Sheets

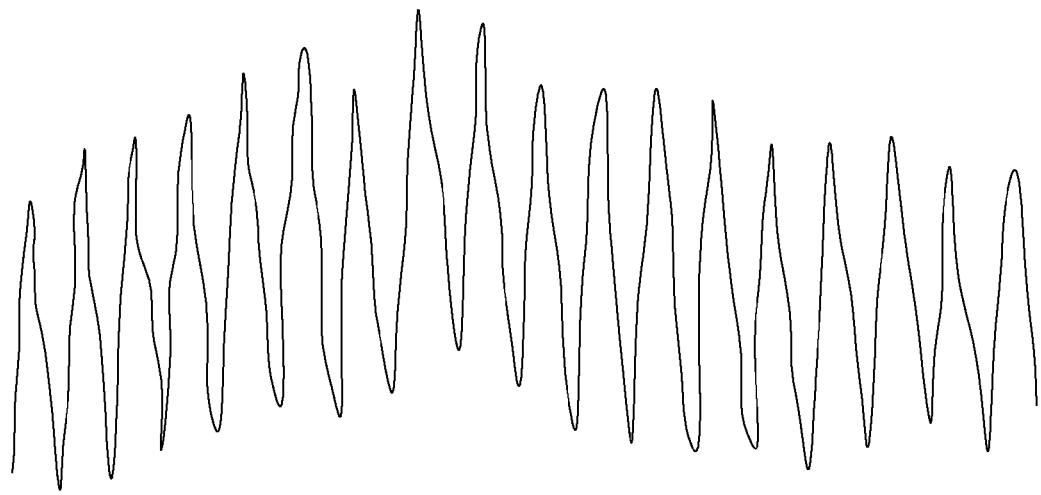
FIG. 1
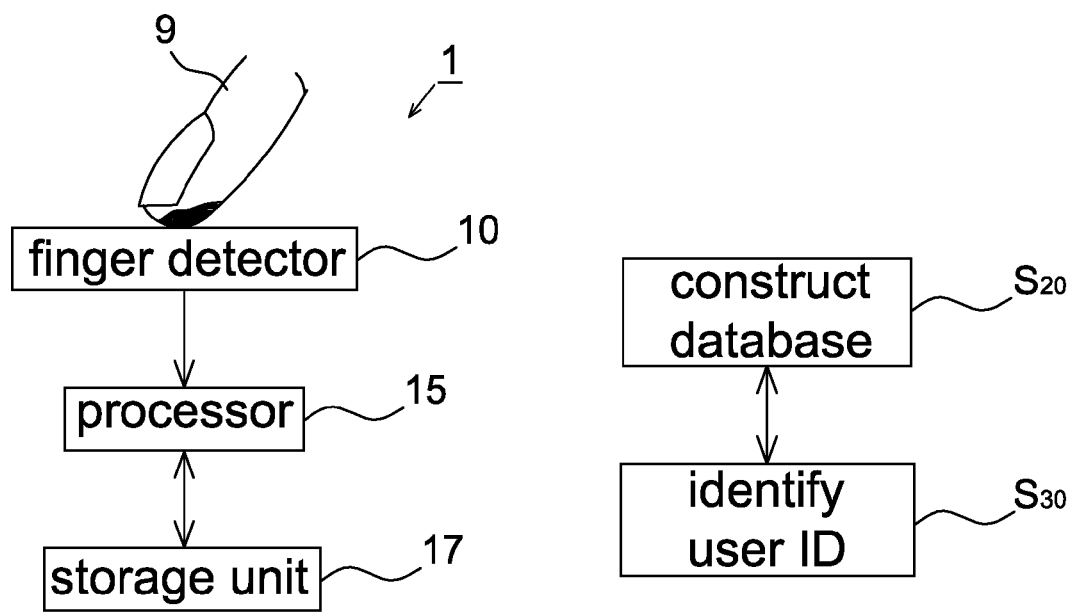
FIG. 2
FIG. 3

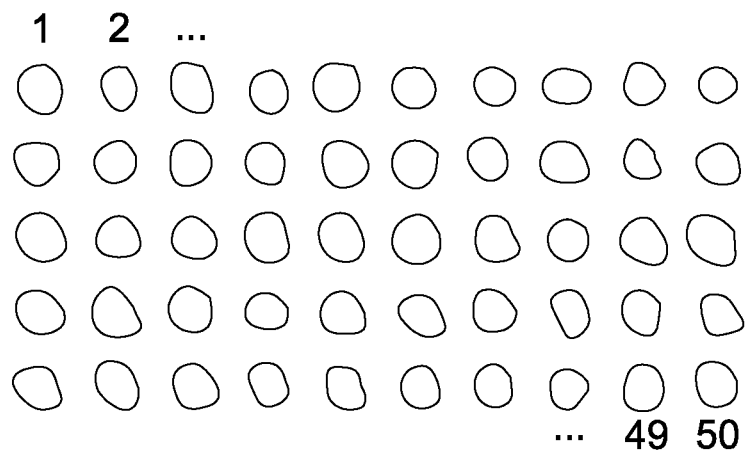
FIG. 4A
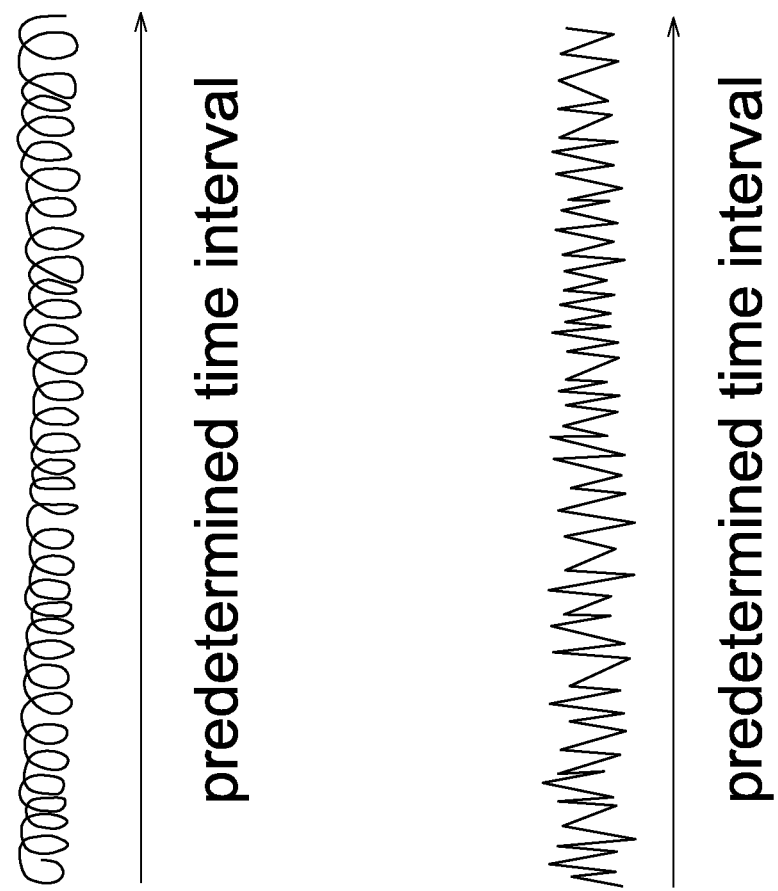
FIG. 4B                    FIG. 4C

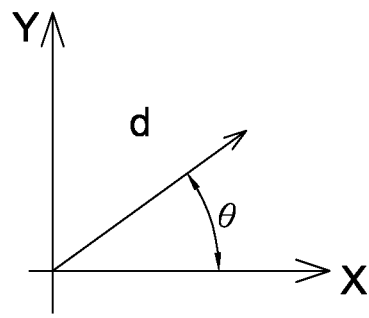
FIG. 5A
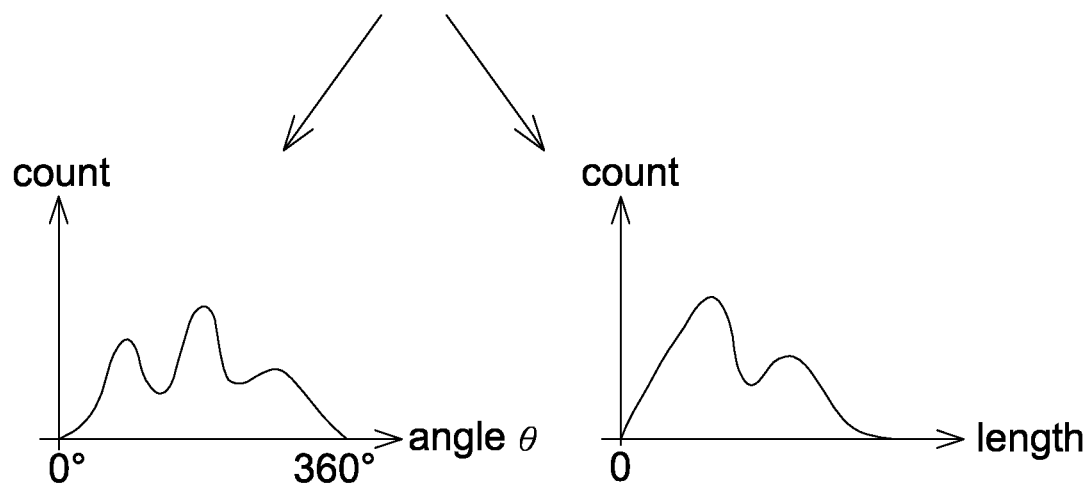
FIG. 5B
FIG. 5C

USER IDENTIFICATION METHOD, PHYSIOLOGICAL DETECTION DEVICE AND PHYSIOLOGICAL DETECTION METHOD

CROSS REFERENCE TO RELATED APPLICATION

This application claims the priority benefit of Taiwan Patent Application Serial Number 101115437, filed on May 1, 2012, the full disclosure of which is incorporated herein by reference.

BACKGROUND

1. Field of the Disclosure

This disclosure generally relates to a detection system and, more particularly, to a physiological detection device, a physiological detection method and a user identification method being used that may automatically identify the user ID.

2. Description of the Related Art

Conventional pulse oximeters utilize a noninvasive method to monitor the blood oxygenation and the heart rate of a user. The conventional pulse oximeters generally emit a red light beam (wavelength of about 660 nm) and an infrared light beam (wavelength of about 910 nm) to penetrate a part of the human body and detects an intensity variation of the penetrating light based on the feature of the oxyhemoglobin and deoxyhemoglobin having different absorptivities in particular spectrum, e.g. referring to U.S. Pat. No. 7,072,701 and entitled "Method for spectrophotometric blood oxygenation monitoring". After the intensity variation of the penetrating light of the two wavelengths are detected, the blood oxygenation can be calculated according to equation (1):

$$\text{Oxygen saturation} = 100 \times \%[HbO_2]/([HbO_2]+[Hb]) \quad (1)$$

wherein $[HbO_2]$ is oxyhemoglobin concentration; and $[Hb]$ is deoxyhemoglobin concentration.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the physiology information, such as the oxyhemoglobin concentration and deoxyhemoglobin concentration respectively. Finally, the blood oxygenation can be calculated according to equation (1).

However, the physiological information can reflect actual conditions of the user only after the measured data is recorded for a long time, but conventional physiological detection devices are not able to automatically identify the current user ID.

Accordingly, the present disclosure provides a physiological detection device, a physiological detection method and a user identification method being used in which the user ID of a current user may be automatically identified and linked to the corresponding database in an initial stage of operation so as to increase the practicality of the physiological detection device.

SUMMARY

The present disclosure provides a user identification method that may be applied to various electronic devices capable of being linked to a user database.

The present disclosure further provides a physiological detection device and a physiological detection method that may automatically detect a user ID at an initial stage of operation and link the user ID to a corresponding database.

The present disclosure provides a user identification method including a step of constructing database and a step of identifying user ID. In the step of constructing database, at least one predetermined track, drawn by at least one user for a predetermined time interval or a predetermined times on a finger detection unit, is analyzed to construct a database containing at least one track feature corresponding the at least one predetermined track drawn by the at least one user. In the step of identifying user ID, a current track drawn by a current user on the finger detection unit is analyzed and the current user is identified according to the track feature stored in the database.

The present disclosure further provides a physiological detection device including a finger detection unit, a storage unit and a processing unit. The finger detection unit is configured to detect a current track drawn by a current user and current physiological information of the current user. The storage unit is configured to previously store track features of predetermined tracks drawn, for a predetermined time interval or a predetermined times on the finger detection unit, by a plurality of users and each of the track features is associated with one of the users. The processing unit is configured to analyze the current track and identify the current user according to the track features stored in the storage unit.

The present disclosure further provides a physiological detection method including the steps of: detecting a current track drawn by a user with a finger detection unit; comparing, using a processing unit, the current track with a track feature previously stored; linking, using the processing unit, to pass physiological information associated with the user; and detecting current physiological information of the user with the finger detection unit.

In the physiological detection device and the physiological detection method of the present disclosure, the track feature includes track angle information and track length information. The processing unit compares a distribution shape of the track angle information and the track length information with a track angle distribution and a track length distribution of the current track so as to identify the current user.

In the physiological detection device and the physiological detection method of the present disclosure, the predetermined track may be a circle, a rectangle, a polygon, a line segment or other shapes that can be analyzed to contain the track feature of the user.

In the physiological detection device and the physiological detection method of the present disclosure, the user ID of a current user may be automatically identified before current physiological information of the current user is identified. The current physiological information may be linked to pass physiological information of the current user such that it is able to record the physiological information of the current user for referencing and increase the credibility of the measured physiological information.

BRIEF DESCRIPTION OF THE DRAWINGS

Other objects, advantages, and novel features of the present disclosure will become more apparent from the following detailed description when taken in conjunction with the accompanying drawings.

FIG. 1 shows a schematic diagram of an intensity variation of the penetrating light detected by a pulse oximeter.

FIG. 2 shows a block diagram of the physiological detection device according to an embodiment of the present disclosure.

FIG. 3 shows two steps of the user identification method according to an embodiment of the present disclosure.

FIGS. 4A-4C show schematic diagrams of the predetermined track drawn by a user in the user identification method according to the embodiment of the present disclosure.

FIGS. 5A-5C show schematic diagrams of the track feature of a predetermined track in the user identification method according to the embodiment of the present disclosure.

DETAILED DESCRIPTION OF THE EMBODIMENT

Figure 6:
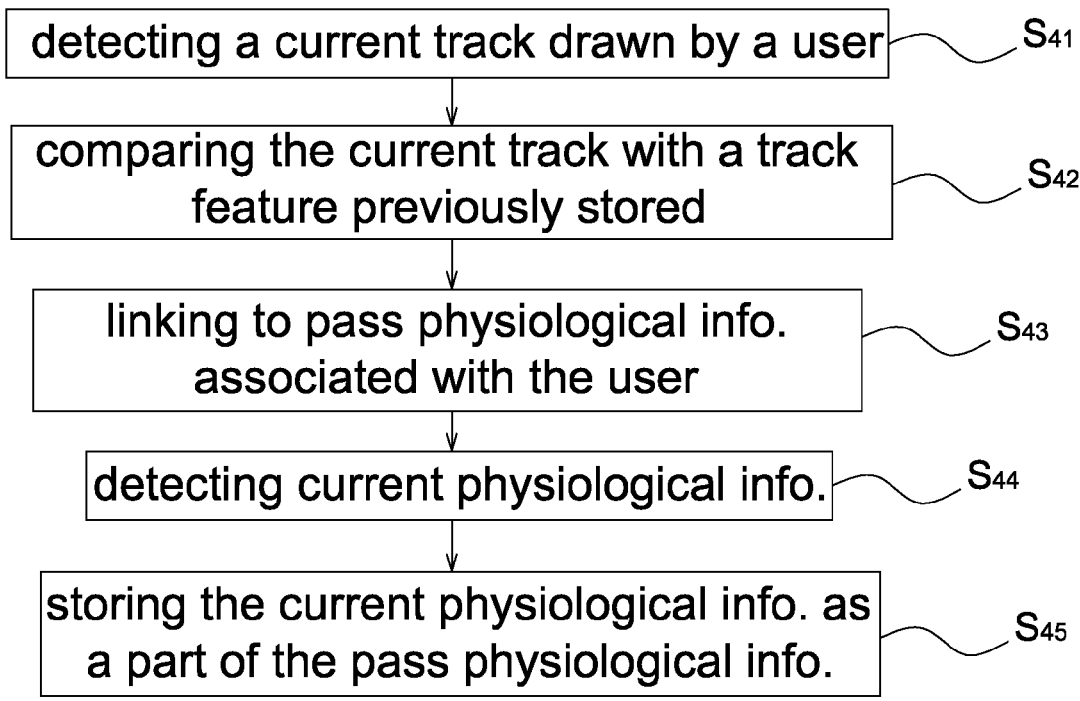
FIG. 6 shows a flow chart of the physiological detection method according to an embodiment of the present disclosure.

It should be noted that, wherever possible, the same reference numbers will be used throughout the drawings to refer to the same or like parts.

Referring to FIG. 2, it shows a schematic block diagram of the physiological detection device 1 according to an embodiment of the present disclosure. The physiological detection device 1 includes a finger detection unit 10, a processing unit 15 and a storage unit 17, wherein the processing unit 15 and storage unit 17 may be included in or separated from the finger detection unit 10.

The finger detection unit 10 may be, for example, an optical finger mouse and configured to detect a current track drawn on the finger detection unit 10 with a finger 9 of a current user and to detect physiological information of the current user, wherein the method that an optical finger mouse detects the current track (e.g. including a moving direction and a moving distance) is well known and the method of detecting the physiological information will be described below with an example. The storage unit 17 is configured to store track features of predetermined tracks drawn, for a predetermined time interval or a predetermined times on the finger detection unit 10, by a plurality of users previously and each of the track features is associated with one of the users. The processing unit 15 is configured to analyze the current track and identify the current user according to the track features stored in the storage unit 17.

Referring to FIG. 3, a user identification method used by the physiological detection device 1 of this embodiment includes at least two steps: a step of constructing database (Step $S_{20}$) and a step of identifying user ID (Step $S_{30}$), wherein the step of constructing database may be performed at any necessary time, e.g. increasing users. In the step of constructing database, a plurality of predetermined tracks, drawn by a plurality of users (one user each time) for a predetermined time interval or a predetermined times on the finger detection unit 10, are analyzed by the processing unit 15 to construct a database containing track features corresponding to the predetermined tracks drawn by each user, wherein the database is stored in the storage unit 17. In the step of identifying user ID, the processing unit 15 analyzes a current track drawn by a current user on the finger detection unit 10 and identifies the current user according to the track features stored in the database. It should be mentioned that the user identification method of this embodiment may be applied to various electronic devices capable of being linked with the user database; and said user database may be a photo database or other digital database.

Referring to FIGS. 4A to 4C, they respectively show an embodiment of constructing a track feature of the predetermined track associated with each of the users in the step of constructing database. In this embodiment, the predetermined time interval may be 10 to 30 seconds and the predetermined times may be 20 to 50 times, wherein an actual time interval and actual times may be determined according to a period for identifying the track feature. For example in FIG. 4A, the users sequentially draw 50 circles to be served as the predetermined track in the step of constructing database. In other embodiments, the predetermined track may be a rectangle, a polygon, a line segment or other tracks which can be analyzed to contain the track feature of the user. For example in FIG. 4B, the users continuously draw the predetermined track substantially having a circle shape for 10 seconds in the step of constructing database. For example in FIG. 4C, the users continuously draw the predetermined track of a plurality of line segments for 10 seconds in the step of constructing database. It should be mentioned that FIGS. 4B and 4C are only exemplary and because the predetermined track is drawn by the users on the finger detection unit 10, the predetermined track is substantially within an area and does not extend toward any specific direction.

Next, the processing unit 15 acquires an angle variation and a length variation between two sampling points in the predetermined track drawn by the users to be served as the track feature. For example referring to FIG. 5A, it shows a schematic diagram of an angle variation $\theta$ and a length variation d between two sampling points in the predetermined track. The processing unit 15 gathers a distribution shape of the angle variation $\theta$ in the predetermined track drawn within the predetermined times or the predetermined time interval to be served as track angle information as shown in FIG. 5B. The processing unit 15 also gathers a distribution shape of the length variation d in the predetermined track drawn within the predetermined times or the predetermined time interval to be served as track length information as shown in FIG. 5C. That is, the track feature includes track angle information and track length information. Finally, the track angle information and the track length information corresponding to different users are classified and stored in the database previously.

In the step of identifying user ID, a current user may draw one or a plurality of current tracks or draw a current track for an identification period on the finger detection unit 10. The processing unit 15 then analyzes a track angle distribution and a track length distribution of the current track (similar to FIGS. 5B and 5C) and compares with the distribution shape of the track angle information and the track length information stored in the database so as to identify the current user. It is appreciated that the current user is one of the users involved in the step of constructing database. The current track and the predetermined track have substantially similar shapes such as circles, rectangles, polygons or line segments.

In the step of identifying user ID, when the current user has been identified, the processing unit 15 then links to pass physiological information of the current user stored in the database for being referred by the current user. Meanwhile, the finger detection unit 10 may start to detect current physiological information of the current user and store the detected current physiological information into the database to be served a part of the pass physiological information.

Referring to FIG. 6, it shows a flow chart of the physiological detection method according to an embodiment of the present disclosure, which includes the steps of: detecting a current track drawn by a user with a finger detection unit (Step $S_{41}$); comparing, using a processing unit, the current track with a track feature previously stored (Step $S_{42}$); linking, using the processing unit, to pass physiological information associated with the user (Step $S_{43}$); detecting current physiological information of the user with the finger detection unit (Step $S_{44}$); and storing the current physiological information as a part of the pass physiological information (Step $S_{45}$). In this embodiment, the storage unit 17 has previously stored at least one track feature formed by analyzing the predetermine track and drawn by at least one user, and the track feature may include track angle information and track length information as shown in FIGS. 5B and 5C.

Step $S_{41}$: A current user uses his or her finger 9 to draw one or a plurality of current tracks or draw a current track for an identification period on the finger detection unit 10. The finger detection unit 10 detects the current track and sends the detected result to the processing unit 15.

Step $S_{42}$: The processing unit 15 analyzes a track angle distribution and a track length distribution of the current track and compares the analyzed result with the track feature, e.g. a distribution shape of track angle information and track length information, previously stored in the storage unit 17 so as to identify the current user, wherein it is able to identify the current user according to the highest similarity of the distribution shapes.

Step $S_{43}$: When the current user has been identified, the processing unit 15 may link to pass physiological information associated with the current user in the database for being reviewed by the current user.

Step $S_{44}$: The finger detection unit 10 may start to detect current physiological information of the current user, e.g. a blood oxygenation and/or a heart rate. It should be mentioned that a sequence of the Steps $S_{43}$ and $S_{44}$ does not limit to that shown in FIG. 6.

Step $S_{45}$: The processing unit 15 may save the detected current physiological information in the database to be served a part of the pass physiological information such that it is able to continuously record the physiological information associated with each user.

An embodiment of the physiological detection device of the present disclosure will be illustrated hereinafter, but the present disclosure is not limited to the embodiment. For example, the physiological detection device of the present disclosure may also be those configured to detect the physiological information according to an intensity variation of the penetrating light, such as conventional pulse oximeters. Since the detection method of a pulse oximeter is well known, details thereof are not described herein. It should be mentioned that an example of detecting the current physiological information and the finger displacement by the physiological detection device 1 according to the embodiment of the present disclosure is described below. When the finger detection device 1 is configured to detect the finger track, it is able to calculate the track feature by using the moving vector between two sampling points.

Figure 7A:
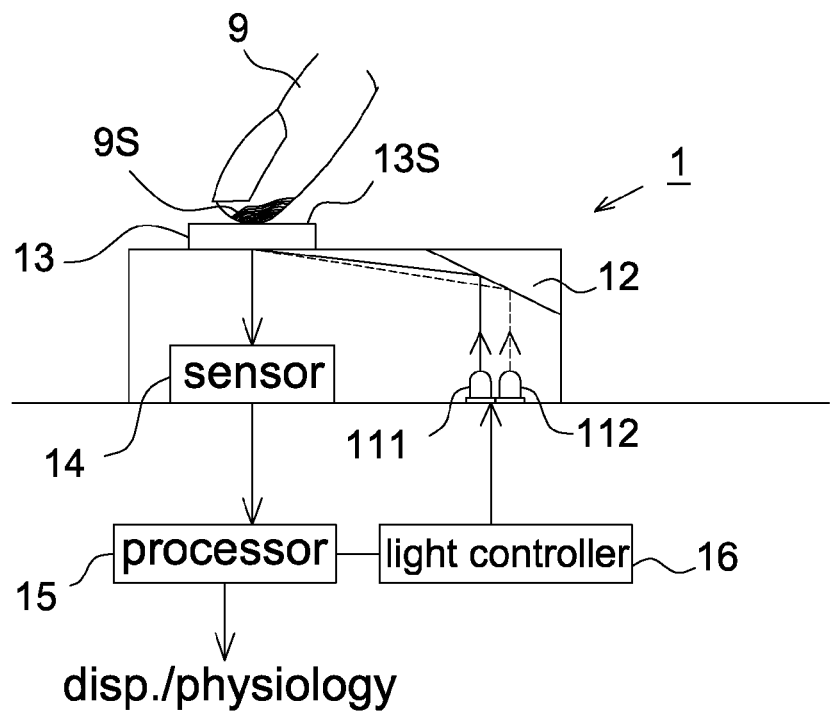
FIG. 7A shows an application example of the physiological detection device according to an embodiment of the present disclosure.

Referring to FIG. 7A, it shows an application example of the physiological detection device 1 according to an embodiment of the present disclosure, such as an optical finger mouse herein. The physiological detection device 1 is configured to detect a displacement and a contact status of a finger 9 of a user with respect to the physiological detection device 1 and to detect physiological information of the user, such as a blood oxygenation and/or a heart rate. Generally, the physiological detection device 1 starts to calculate the displacement and the physiological information when identifying that the contact status is a touch state.

The physiological detection device 1 includes two light sources 111 and 112, a light guide 12, a touch member 13, an image sensor 14, a processing unit 15 and a light control unit 16; in FIG. 7A, a spatial relationship between every component is only exemplary and not to limit the present disclosure. The two light sources 111 and 112 may be light emitting diodes or laser diodes to respectively emit light of different wavelengths. Preferably, said different wavelengths are two wavelengths used in conventional pulse oximeters, such as red light of wavelength about 660 nm and infrared light of wavelength about 905, 910 or 940 nm. It is appreciated that the wavelengths mentioned herein are the center wavelength of corresponding spectrum.

The light guide 12 is configured to direct the light emitted by the light sources 111 and 112 to the touch member 13. The light guide 12 is not limited to a reflecting surface and it may allow the light emitted by the light sources 111 and 112 to transmit to the touch member 13 by propagating therein. In other embodiments, if the light emitted from the light sources 111 and 112 can directly impinge on the touch member 13, the light guide 12 may not be implemented.

The touch member 13 has a touch surface 13S for the finger 9 to operate thereon, and the touch member 13 is preferably transparent to the light emitted by the light sources 111 and 112. When the finger 9 approaches or touches the touch surface 13S, the light emitted by the light sources 111 and 112 is reflected.

The image sensor 14 receives, with a sampling parameter, reflected light from the touch member 13 (more specifically from the finger surface 9S) so as to generate a plurality of image frames, which may have a size of 16×16, wherein the sampling parameter may include an exposure time and an image gain, but not limited thereto. It is appreciated that FIG. 7A may further include lens or lens set configured to direct the reflected light to the image sensor 14 so as to improve the sensing efficiency of the image sensor 14. The image sensor 14 is preferably an active matrix sensor, e.g. a CMOS image sensor, but it may be other devices for detecting images.

The processing unit 15 calculates a displacement and a contact status of the finger 9 with respect to the touch surface 13S and physiological information of a user according to the image frames from the image sensor 14. The displacement, contact status and physiological information obtained by the processing unit 15 may be sent to an electronic device having a response device for displaying or corresponding control, wherein the response device may be a display device, a lamp device, a seven-segment display or a sound device. The electronic device may be a portable electronic device or a home appliance.

The light control unit 16 is coupled to the processing unit 15 and configured to control the ON/OFF (i.e. on-states and off-states) of the light sources 111 and 112 in correspondence with the image capturing of the image sensor 14, and details thereof will be illustrated hereinafter.

Figure 7B:
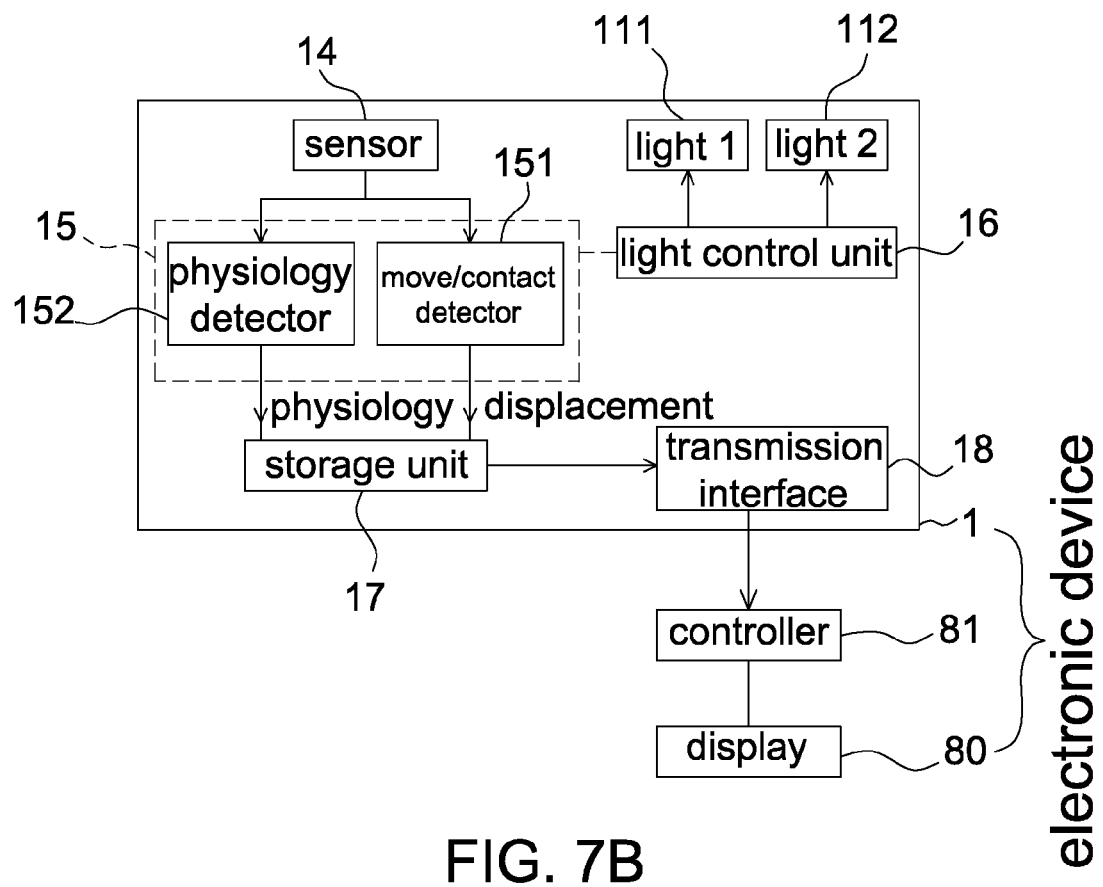
FIG. 7B shows a schematic block diagram of the application example of the physiological detection device shown in FIG. 7A.

Please refer to FIGS. 7A and 7B, FIG. 7B shows a schematic block diagram of the physiological detection device 1 according to an embodiment of the present disclosure. The physiological detection device 1 includes a first light source 111, a second light source 112, the image sensor 14, the processing unit 15, the light control unit 16, a storage unit 17 and a transmission interface 18, wherein because the processing unit 15 is configured to perform multifunction calculation, the processing unit 15 may include a move/contact detection unit 151 configured to detect the displacement and contact status of the finger 9 with respect to the touch surface 13S and a physiology detection unit 152 configured to detect the physiological information of the user. That is, the processing unit 15 may be a single element or be composed of two elements. The first light source 111 may emit red light of wavelength about 660 nm and the second light source 112 may emit infrared light of wavelength about 905, 910 or 940 nm. Broadly speaking, the first light source 111 and the second light source 112 respectively emit light of two wavelengths used in conventional pulse oximeters. Functions of the image sensor 14 and the light control unit 16 have been illustrated above and thus details thereof are not repeated herein. The storage unit 17 is configured to store the displacement, contact status, physiological information, track features obtained by the processing unit 15 and various parameters needed in calculation. The transmission interface 18 is configured to wired or wirelessly transmit the displacement, contact status and physiological information stored in the storage unit 17 to a controller 81, wherein the technology of wired and wireless communication is well known and thus details thereof are not described herein. The controller 81 may be disposed inside or outside an electronic device having a response device 80 and configured to control the electronic device to display and/or respond the received displacement, contact status and physiological information through the response device 80.

In one embodiment, the physiological detection device 1, the controller 81 and response device 80 may compose an electronic device, e.g. a TV, a projection device or a computer system and the physiological detection device 1 may be disposed inside the controller 81, wherein the controller 81 may be a remote controller, a mouse, a keyboard, an optical distance measuring device or other computer peripheral devices. In other words, the physiological detection device 1, the controller 81 and the response device 80 may be coupled together wired or wirelessly so as to form a single device (e.g. a portable electronic device) or a plurality of devices physically separated from each other (e.g. a home appliance).

Therefore, the physiological detection device 1 of the present disclosure may incorporate with an electronic device having a response device 80 such that when a user controls a cursor shown on the response device 80 or a software executed by the electronic device through the physiological detection device 1, the response device 80 may simultaneously show the physiological information (e.g. including current physiological information and pass physiological information) of the user for reference. And when the physiological information indicates that the user is in a fatigue state (e.g. according to a value of the physiological information), a warning can be issued, wherein the method of showing the physiological information and the warning may be performed by, for example, showing on a screen, representing by a lamp device or by sound controlled by a software.

In other embodiments, the physiological detection device 1 may include two image sensors configured to respectively detect light of two different wavelengths, wherein an optical bandpass filter may be integrated with one or two of the image sensors in order to select the desired spectrum.

Sampling Mechanism

The physiological detection device 1 of the present disclosure includes two light sources and may execute two functions simultaneously, wherein the detection function of the displacement and contact status does not need to use the image frames associated with specific wavelength, but the detection function of the physiological information needs to be performed respectively corresponding to the image frames of different wavelengths. First, the sampling mechanism of the image frames in the present disclosure is illustrated.

Figure 8:
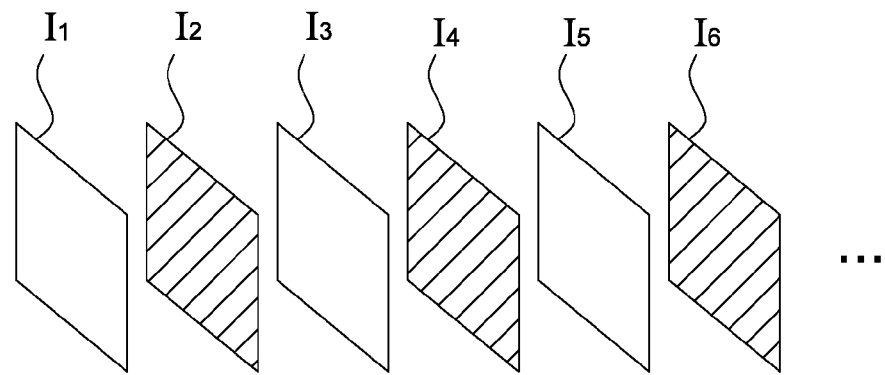
FIG. 8 shows a schematic diagram of the image frames captured by the image sensor in the application example of the physiological detection device shown in FIG. 7A.

In one embodiment, the light control unit 16 controls the first light source 111 and the second light source 112 to light alternatively. The image sensor 14 captures image frames with a high and fixed sampling frequency (e.g. 3000 frames/sec) and synchronizing to the lighting (i.e. the on-state) of the first light source 111 or the second light source 112, and outputs a plurality of image frames $I_1$ to $I_6$ . . . , as shown in FIG. 8, to the processing unit 15 (or simultaneously outputs the image frames to the move/contact detection unit 151 and the physiology detection unit 152), wherein the image frames $I_1$ to $I_6$ . . . include first image frames $I_1, I_3, I_5$ . . . corresponding to the on-state of the first light source 111 and second image frames $I_2, I_4, I_6$ . . . corresponding to the on-state of the second light source 112.

The processing unit 15 (or the move/contact detection unit 151) may identify a contact status and calculate a displacement according to the first and second image frames $I_1$ to $I_6$ . . . , e.g. identifying whether the finger 9 approaches or touches the touch surface 13S according to a comparison result of comparing a brightness value of the first and second image frames with at least one brightness threshold, wherein when the brightness value of the image frames is larger than or smaller than the brightness threshold, the system enters a touch state. After entering the touch state, the processing unit 15 may calculate the displacement according to the correlation between two first image frames, between one first image frame and one second image frame, or between two second image frames. It should be mentioned that although the method of identifying the contact status and calculating the displacement may use conventional methods, the identification and the calculation in the present disclosure need to use the image frames corresponding to the reflected light of two different wavelengths.

The processing unit 15 (or the physiology detection unit 152) may calculate an intensity variation of first image frame according to the first image frames $I_1, I_3, I_5$ . . . , calculate an intensity variation of second image frame according to the second image frames $I_2, I_4, I_6$ . . . (described later), and accordingly calculate the absorption ratio at two different spectra so as to obtain [$HbO_2$] and [Hb]. Finally, the blood oxygenation may be calculated according to equation (1), and the heart rate may also be calculated according to a comparison result of comparing the intensity variation of the first image frames and/or the second image frames with at least one pulse threshold.

In another embodiment, the light control unit 16 controls the first light source 111 and the second light source 112 to light simultaneously and synchronizing to the image capturing of the image sensor 14; that is, the image sensor 14 may receive reflected light of two wavelengths simultaneously. Therefore, in this embodiment an optical filter is further disposed in front of at least a part of a sensing surface of the image sensor 14, wherein the optical filter may be an optical bandpass filter to allow the part of the sensing surface behind the optical filter to only receive the spectrum of the first light source 111 or the second light source 112, such that the processing unit 15 (or the move/contact detection unit 151 and the physiology detection unit 152) may distinguish the first image frame (i.e. the part of the image frame associated with the reflected light of the first light source 111) and the second image frame (i.e. the part of the image frame associated with the reflected light of the second light source 112).

In this manner, the processing unit 15 (or the move/contact detection unit 151) may also calculate a contact status and a displacement according to the first image frames and the second image frames $I_1$ to $I_6$ . . . . The processing unit 15 (or the physiology detection unit 152) may also calculate the intensity variation of first image frame according to the first image frames $I_1, I_3, I_5$ . . . , calculate the intensity variation of second image frame according to the second image frames $I_2, I_4, I_6$ . . . , and calculate the blood oxygenation and the heart rate according to the two intensity variations.

In the present disclosure, the light control unit 16 is configured to control the on-states (lighting) and off-states (not lighting) of the first light source 111 and the second light source 112; the image sensor 14 captures, at a sampling frequency, reflected light from the finger 9 to generate a plurality of first image frames corresponding to the on-state of the first light source and a plurality of second image frames corresponding to the on-state of the second light source; and the processing unit 15 calculates the contact status, displacement and physiological information according to the first image frames and the second image frames.

Calculating Physiology Information

Corresponding to the on-states of different light sources, the image frames captured by the image sensor 14 may contain physiology information and movement information at the same time. Therefore, in the present disclosure the processing unit 15 (or the physiology detection unit 152) has to separate two types of information at first and then is able to calculate the physiological information correctly. In the present disclosure, the processing unit 15 may separate the two types of information according to, for example, independent component analysis (ICA) or blind source separation (BSS).

Figure 9:
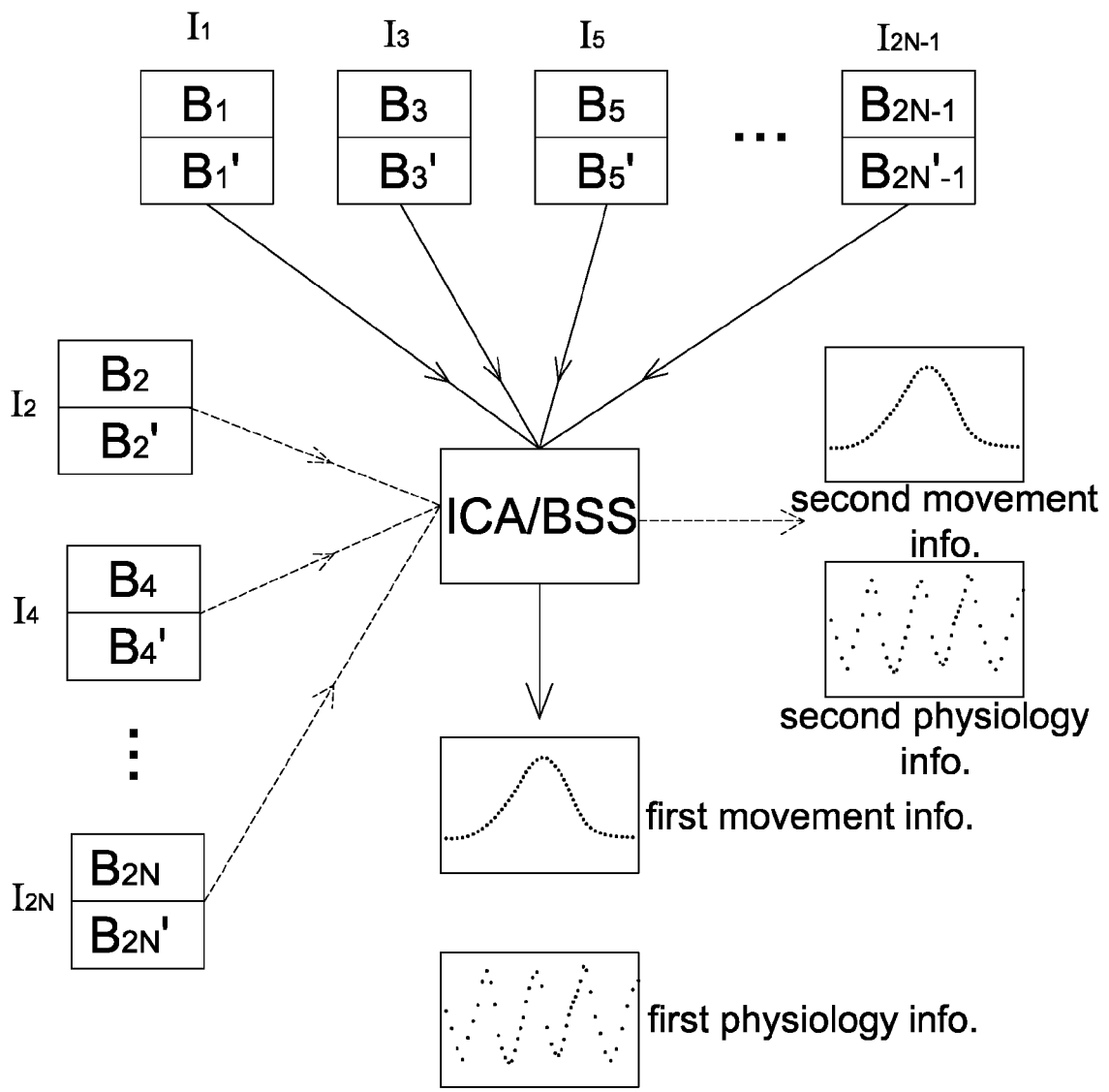
FIG. 9 shows a schematic diagram of the separation of the movement information and the physiology information in the application example of the physiological detection device shown in FIG. 7A.

Please refer to FIGS. 8 and 9, first taking the first image frames $I_1, I_3, I_5$ . . . shown in FIG. 8 as an example, each of the first image frames or each of the sum (or average) of a plurality of first image frames is divided into at least two parts and an average brightness of each part is calculated, e.g. the image frame $I_1$ is divided into two parts respectively having an average brightness $B_1$ and $B_1'$; the image frame $I_3$ is divided into two parts respectively having an average brightness $B_3$ and $B_3'$; . . . ; the image frame $I_{2N-1}$ is divided into two parts respectively having an average brightness $B_{2N-1}$ and $B_{2N-1}'$, wherein the image frames may be divided into more than two parts in other embodiments. Next, first movement informant and first physiology information is separated from the divided first image frames according to independent component analysis (ICA) or blind source separation (BSS) method as shown in FIG. 9, and both information is shown as a curve of intensity variation. In the present disclosure the movement information is abandoned and the physiology information is kept. It is appreciated that as the sampling frequency of the image sensor 14 is much higher than the heart rate, the separated physiology information is shown as a curve of the intensity variation corresponding to the pulse beating (similar to FIG. 1), and the separated movement information is not limited to that shown in FIG. 9. In addition, the two parts divided from the image frames are not necessary to be the upper and lower parts of the image frames. In addition, as it is necessary to respectively calculate the physiological information of two different wavelengths, the aforementioned separation process is performed respectively on the first image frames $I_1, I_3, I_5$ . . . $I_{2N-1}$ (i.e. corresponding to the on-state of the first light source) and the second image frames $I_2, I_4, I_6$ . . . $I_{2N}$ (i.e. corresponding to the on-state of the second light source). It should be mentioned that, if the information separation is performed on the sum or average of the image frames, each of the $I_1$ to $I_{2N-1}$ and $I_2$ to $I_{2N}$ shown in FIG. 9 represents a sum or an average of M image frames.

It should be mentioned that the displacement and the contact status of the finger 9 are calculated by the processing unit 15 (or the move/contact detection unit 151) directly according to the original first image frames and second image frames and not according to the separated movement information. The ICA and BSS methods are mainly configured to separate combined signals so as to eliminate the signal noise caused by finger movement.

In the present disclosure, the processing unit 15 further calculates a heart rate according to a comparison result of comparing at least one pulse threshold with the first intensity variation (i.e. the first physiology information) and/or the second intensity variation (i.e. second physiology information). In addition, in calculating the predetermined track and the current track, it is able to activate one of the two light sources without activating both light sources simultaneously.

In a word, the physiological detection method of the present disclosure includes the steps of: providing light of a first wavelength and a second wavelength to a finger surface; capturing reflected light of the first wavelength to generate a plurality of first image frames and capturing reflected light of the second wavelength to generate a plurality of second image frames; dividing each of the first image frames and the second image frames into at least two parts and calculating an average brightness of each part; using independent component analysis or blind source separation to analyze the average brightness of the each part of the first image frames to obtain a first intensity variation and to analyze the average brightness of the each part of the second image frames to obtain a second intensity variation; and calculating a physiological information according to the first intensity variation and the second intensity variation. The physiological detection method of this embodiment is suitable for an electronic device having an optical finger mouse and preferably including a response device.

In addition, the physiological detection device 1 of the present disclosure may be formed as a module and configured to output coded and/or sequenced finger and physiological information. In addition, the physiological detection device 1 of the present disclosure may only be configured to detect image frames and the image frames or a sum of the image frames may be sent to a host for calculating the finger and physiological information; that is, the processing unit 15 may be included in a host exterior to the physiological detection device 1. In addition, the physiological detection device 1 of the present disclosure may also cooperate with other electronic devices, such as an optical mouse, a keyboard, a remote controller or an optical distance detection device.

The physiological detection device and the physiological detection method of the present disclosure may include other mechanisms to increase the detection accuracy, for example, (1) calculating a sum of a plurality of image frames to increase the signal-to-noise ratio (SNR); (2) normalizing the image frame with a sampling parameter, e.g. an exposure time and/or an image gain, so as to eliminate the interference from different sampling parameters; (3) correcting the system frequency by using an external light source having an accurate lighting frequency as a reference frequency; (4) calculating a differential image of a bright image frame, which corresponds to the turning on the light source, and a dark image, which corresponds to the turning off the light source, so as to eliminate the interference from ambient light; and (5) stop calculating the physiological information when the displacement of an object to be detected is larger than a predetermined value so as not to obtain error information. In addition, in order to save the system power, the physiological detection device of the present disclosure may automatically enter a sleep mode when it is idle for a predetermined time interval. The above mentioned mechanisms may be performed by the processing unit 15.

As mentioned above, conventional pulse oximeters are used to detect the physiological information of a single user and not equipped with the function of identifying the user ID. Therefore, the present disclosure further provides a physiological detection device (FIG. 2) a physiological detection method (FIG. 6) and a user identification method being used (FIG. 3) that may automatically detect a user ID in an initial stage of operation and the user ID is linked to an associated database so as to increase the practicality of the physiological detection device.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A user identification method, comprising:
 a step of constructing database in which at least one predetermined track, drawn by at least one user for a predetermined time interval or a predetermined times on a finger detection unit, is analyzed to construct a database containing at least one track feature corresponding to the at least one predetermined track drawn by the at least one user; and a step of identifying user in which a current track drawn by a current user on the finger detection unit is analyzed and the current user is identified according to the track feature in the database; wherein after the step of identifying user ID the method further comprises: detecting current physiological information of the current user with the finger detection unit; and storing the current physiological information to the database.

2. The user identification method as claimed in claim 1, wherein the track feature comprises track angle information and track length information.

3. The user identification method as claimed in claim 2, wherein in the step of identifying user, a distribution shape of the track angle information and the track length information is compared with a track angle distribution and a track length distribution of the current track.

4. The user identification method as claimed in claim 1, wherein after the step of identifying user the method further comprises: linking to pass physiological information of the current user in the database.

5. The user identification method as claimed in claim 1, wherein the predetermined track is a circle, a rectangle, a polygon or a line segment.

6. A physiological detection device, comprising:
 a finger detection unit configured to detect a current track drawn by a current user and current physiological information of the current user;
 a storage unit configured to previously store track features of predetermined tracks drawn, for a predetermined time interval or a predetermined times on the finger detection unit, by a plurality of users and each of the track features is associated with one of the users; and
 a processing unit configured to analyze the current track and identify the current user according to the track features in the storage unit.

7. The physiological detection device as claimed in claim 6, wherein the current physiological feature comprises at least one of a blood oxygenation and a heart rate.

8. The physiological detection device as claimed in claim 6, wherein the finger detection unit is an optical finger mouse.

9. The physiological detection device as claimed in claim 6, wherein the track feature comprises track angle information and track length information.

10. The physiological detection device as claimed in claim 9, wherein the processing unit compares a distribution shape of the track angle information and the track length information with a track angle distribution and a track length distribution of the current track so as to identify the current user.

11. The physiological detection device as claimed in claim 6, wherein the predetermined track is a circle, a rectangle, a polygon or a line segment.

12. A physiological detection method, comprising:
 detecting a current track drawn by a user with a finger detection unit;
 comparing, using a processing unit, the current track with a track feature previously stored;
 linking, using the processing unit, to pass physiological information associated with the user; and
 detecting current physiological information of the user with the finger detection unit.

13. The physiological detection method as claimed in claim 12, further comprising:
 storing the current physiological information as a part of the pass physiological information.

14. The physiological detection method as claimed in claim 12, wherein the pass physiological information and the current physiological information comprise at least one of a blood oxygenation and a heart rate.

15. The physiological detection method as claimed in claim 12, wherein the track feature comprises track angle information and track length information.

16. The physiological detection method as claimed in claim 15, wherein in the step of comparing the current track with a track feature, the processing unit compares a distribution shape of the track angle information and the track length information with a track angle distribution and a track length distribution of the current track.

17. The physiological detection method as claimed in claim 12, wherein the predetermined track is a circle, a rectangle, a polygon or a line segment.

* * * * *